(12) United States Patent
McKenna

(10) Patent No.: US 8,319,401 B2
(45) Date of Patent: Nov. 27, 2012

(54) AIR MOVEMENT ENERGY HARVESTING WITH WIRELESS SENSORS

(75) Inventor: Edward M. McKenna, Boulder, CO (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 158 days.

(21) Appl. No.: 12/771,803

(22) Filed: Apr. 30, 2010

(65) Prior Publication Data
US 2011/0270043 A1   Nov. 3, 2011

(51) Int. Cl.
*H01L 41/09* (2006.01)
*A61B 5/00* (2006.01)
*F03D 9/00* (2006.01)

(52) U.S. Cl. .......... 310/339; 600/300; 600/301; 290/55

(58) Field of Classification Search .............. 600/300, 600/301; 290/55; 300/339
See application file for complete search history.

(56) References Cited

U.S. PATENT DOCUMENTS

| | | | |
|---|---|---|---|
| 3,721,813 A | 3/1973 | Condon et al. |
| 4,971,062 A | 11/1990 | Hasebe et al. |
| 4,974,591 A | 12/1990 | Awazu et al. |
| 5,028,787 A | 7/1991 | Rosenthal et al. |
| 5,035,243 A | 7/1991 | Muz |
| 5,065,749 A | 11/1991 | Hasebe et al. |
| 5,084,327 A | 1/1992 | Stengel |
| 5,094,240 A | 3/1992 | Muz |
| 5,275,159 A | 1/1994 | Griebel |
| 5,348,003 A | 9/1994 | Caro |
| 5,429,129 A | 7/1995 | Lovejoy et al. |
| 5,465,714 A | 11/1995 | Scheuing |
| 5,474,065 A | 12/1995 | Meathrel et al. |
| 5,483,646 A | 1/1996 | Uchikoga |
| 5,511,546 A | 4/1996 | Hon |
| 5,619,992 A | 4/1997 | Guthrie et al. |
| 5,666,952 A | 9/1997 | Fuse et al. |
| D393,830 S | 4/1998 | Tobler et al. |
| 5,779,631 A | 7/1998 | Chance |
| 5,871,442 A | 2/1999 | Madarasz et al. |
| 6,006,120 A | 12/1999 | Levin |

(Continued)

FOREIGN PATENT DOCUMENTS

DE    3516338    11/1986

(Continued)

OTHER PUBLICATIONS

Crilly, et al.; "An Integrated Pulse Oximeter System for Telemedicine Applications," *IEEE Instrumentation and Measurement Technology Conference*, May 19-21, 1997; pp. 102-104; Ottawa, Canada.

(Continued)

*Primary Examiner* — Thomas Dougherty
(74) *Attorney, Agent, or Firm* — Fletcher Yoder

(57) ABSTRACT

A system and method for generating power when one or more motion sensitive structures are moved via airflow. The system may include one or more sensing components which, acting alone or in combination, are capable of generating data related to one or more physiological parameters. The system may also include wireless communication circuitry capable of wirelessly transmitting the data related to the one or more physiological parameters. Furthermore, at least one of the one or more sensing components or the wireless communication circuitry may be at least partially powered, directly or indirectly, by the one or more motion sensitive structures when acted upon by airflow.

22 Claims, 5 Drawing Sheets

U.S. PATENT DOCUMENTS

| | | | |
|---|---|---|---|
| 6,081,742 A | 6/2000 | Amano et al. | |
| 6,144,444 A | 11/2000 | Haworth et al. | |
| 6,261,236 B1 | 7/2001 | Grimblatov | |
| 6,285,895 B1 | 9/2001 | Ristolainen et al. | |
| 6,353,750 B1 | 3/2002 | Kimura et al. | |
| 6,419,671 B1 | 7/2002 | Lemberg | |
| 6,461,305 B1 | 10/2002 | Schnall | |
| 6,512,937 B2 | 1/2003 | Blank et al. | |
| 6,564,088 B1 | 5/2003 | Soller et al. | |
| 6,589,172 B2 | 7/2003 | Williams et al. | |
| 6,591,122 B2 | 7/2003 | Schmitt | |
| 6,791,689 B1 | 9/2004 | Weckström | |
| 6,793,654 B2 | 9/2004 | Lemberg | |
| 6,822,343 B2 * | 11/2004 | Estevez | 290/1 R |
| 6,916,289 B2 | 7/2005 | Schnall | |
| 6,971,580 B2 | 12/2005 | Zhu et al. | |
| 6,992,751 B2 | 1/2006 | Okita et al. | |
| 7,170,201 B2 * | 1/2007 | Hamel et al. | 307/151 |
| 7,198,778 B2 | 4/2007 | Achilefu et al. | |
| 7,236,811 B2 | 6/2007 | Schmitt | |
| 7,313,427 B2 | 12/2007 | Benni | |
| 7,382,247 B2 | 6/2008 | Welch et al. | |
| 7,469,158 B2 | 12/2008 | Cutler et al. | |
| 7,572,229 B2 | 8/2009 | Yeo et al. | |
| 7,574,244 B2 | 8/2009 | Eghbal et al. | |
| 7,649,305 B2 * | 1/2010 | Priya et al. | 310/339 |
| 7,982,370 B2 * | 7/2011 | Wang et al. | 310/339 |
| 7,982,371 B1 * | 7/2011 | Anand et al. | 310/339 |
| 8,092,234 B2 * | 1/2012 | Friedhof et al. | 439/76.1 |
| 2004/0098009 A1 | 5/2004 | Boecker et al. | |
| 2005/0065414 A1 | 3/2005 | Allen et al. | |
| 2005/0075550 A1 | 4/2005 | Lindekugel | |
| 2005/0113656 A1 | 5/2005 | Chance | |
| 2005/0177034 A1 | 8/2005 | Beaumont | |
| 2005/0197548 A1 | 9/2005 | Dietiker | |
| 2005/0234317 A1 | 10/2005 | Kiani | |
| 2005/0280531 A1 | 12/2005 | Fadem et al. | |
| 2006/0058594 A1 | 3/2006 | Ishizuka et al. | |
| 2006/0247501 A1 | 11/2006 | Ali | |
| 2006/0282001 A1 | 12/2006 | Noel et al. | |
| 2007/0049842 A1 | 3/2007 | Hill et al. | |
| 2007/0073121 A1 | 3/2007 | Hoarau et al. | |
| 2007/0100218 A1 | 5/2007 | Sweitzer et al. | |
| 2007/0100219 A1 | 5/2007 | Sweitzer et al. | |
| 2007/0106133 A1 | 5/2007 | Satchwell et al. | |
| 2007/0276273 A1 | 11/2007 | Watson, Jr. | |
| 2008/0146892 A1 * | 6/2008 | LeBoeuf et al. | 600/300 |
| 2008/0281168 A1 | 11/2008 | Gibson et al. | |

FOREIGN PATENT DOCUMENTS

| | | |
|---|---|---|
| DE | 3703458 | 8/1988 |
| EP | 0127947 | 12/1984 |
| EP | 0531631 | 3/1993 |
| JP | 5049625 | 3/1993 |
| JP | 6014906 | 1/1994 |
| JP | 6269430 | 9/1994 |
| JP | 7236625 | 9/1995 |
| JP | 2000237170 | 9/2000 |
| JP | 2004159810 | 6/2004 |
| JP | 2004329406 | 11/2004 |
| JP | 2004337605 | 12/2004 |
| JP | 2004351107 | 12/2004 |
| WO | WO8909566 | 10/1989 |
| WO | WO9111137 | 8/1991 |
| WO | WO9947039 | 9/1999 |
| WO | WO2004084720 | 10/2004 |
| WO | WO2005010568 | 2/2005 |
| WO | WO2005114524 | 12/2005 |
| WO | WO2006079862 | 8/2006 |
| WO | WO2006109072 | 10/2006 |
| WO | WO2007015833 | 2/2007 |
| WO | WO2007071180 | 6/2007 |
| WO | WO2007141121 | 12/2007 |

OTHER PUBLICATIONS

Warren, et al.; "Wearable Sensors and Component-Based Design for Home Health Care," *Proceedings of the Second Joint EMBS-BMES Conference*, Oct. 23-26, 2002; pp. 1871-1872; Houston, Texas.

Lebak, et al.; "Implementation of a Standards-Based Pulse Oximeter on a Wearable, Embedded Platform," *Proceeding of the 25$^{th}$ Annual International Conference of the IEEE EMBS*, Sep. 17-21, 2003; pp. 3196-3198; Cancun, Mexico.

Nagl, et al.; "Wearable Sensor System for Wireless State-of-Health Determination in Cattle," *Proceeding of the 25$^{th}$ Annual International Conference of the IEEE EMBS*, Sep. 17-21, 2003; pp. 3012-3015; Cancun, Mexico.

Pujary, et al.; "Photodetector Size Considerations in the Design of a Noninvasive Reflectance Pulse Oximeter for Telemedicine Applications," *IEEE*, 2003, pp. 148-149.

Wendelken et al.; "The Feasibility of Using a Forehead Reflectance Pulse Oximeter for Automated Remote Triage," *IEEE*, 2004, pp. 180-181.

Park; "Overview of Energy Harvesting Systems (for low-power electronics)"; The First Engineering Institute Workshop; Energy Harvesting; Jun. 28, 2005; slides 1-30; Los Alamos National Laboratory.

Qin et al; "Microfibre-nanowire hybrid structure for energy scavenging", Nature, Feb. 14, 2008, pp. 809-814; vol. 451, Nature Publishing Group.

* cited by examiner

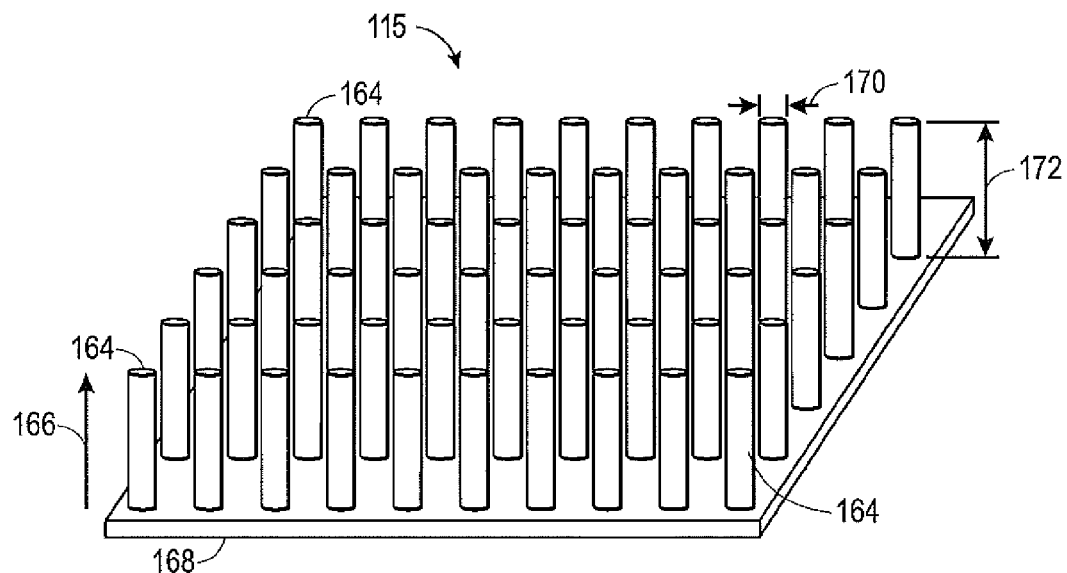
FIG. 3
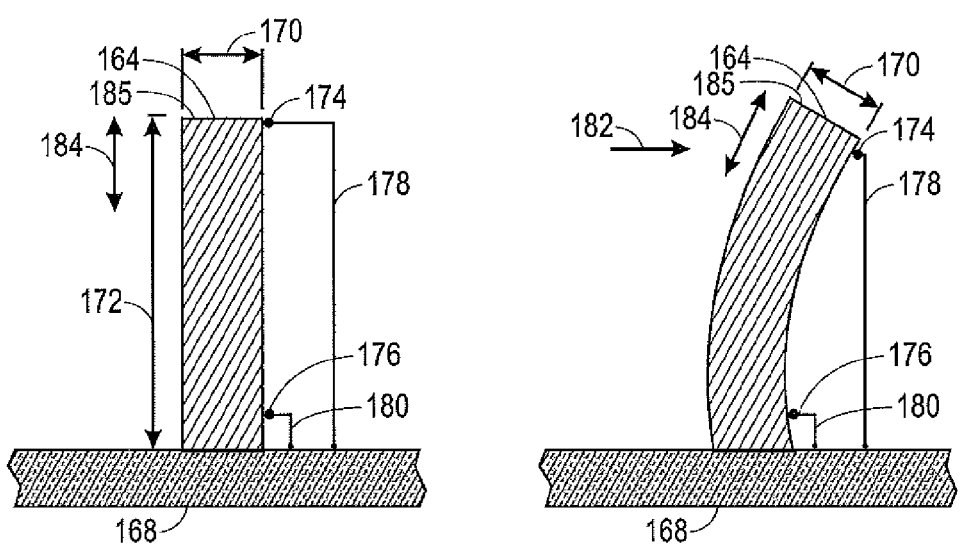
FIG. 4A
FIG. 4B

AIR MOVEMENT ENERGY HARVESTING WITH WIRELESS SENSORS

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Wireless sensors have been developed for use in measuring physiological parameters of a patient. Powering of these devices may present a challenge as there are no wires connected to the sensor available to provide power to the sensors. While internal power sources such as batteries may be utilized, problems may exist in which the internal power source is drained, yielding an undesirable operational lifetime. Accordingly, alternate powering methods may be useful.

BRIEF DESCRIPTION OF THE DRAWINGS

Advantages of the disclosed techniques may become apparent upon reading the following detailed description and upon reference to the drawings in which:

FIG. 3 illustrates the charging device of FIG. 1, in accordance with an embodiment;

FIG. 4A illustrates a piezoelectric element of the charging device of FIG. 1 in a first position, in accordance with an embodiment;

FIG. 4B illustrates a piezoelectric element of the charging device of FIG. 1 in a second position, in accordance with an embodiment;

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to a system and method for converting air movement into power for powering electronic devices. The system may include one or more air motion sensitive structures, that when moved, may generate electromagnetic charging signals. The system may further include one or more elements that may receive the generated electromagnetic charging signals and may utilize the electromagnetic charging signals to charge a power source, such as a rechargeable battery, of a device. Additionally and/or alternatively, the electromagnetic charging signals may be utilized to power the device directly. The device may include, but is not limited to, pulse oximetry sensors, pulse oximetry monitors, portable pulse oximeters, and/or other medical devices. That is, the system may include a device with one or more sensing components which, acting alone or in combination, are capable of generating data related to one or more physiological parameters. The system may also include wireless communication circuitry capable of wirelessly transmitting the data related to the one or more physiological parameters. In one embodiment, at least one of the one or more sensing components or the wireless communication circuitry of the device may be at least partially powered, directly or indirectly, by energy harvested through movement by one or more of the motion sensitive structures.

Figure 1:
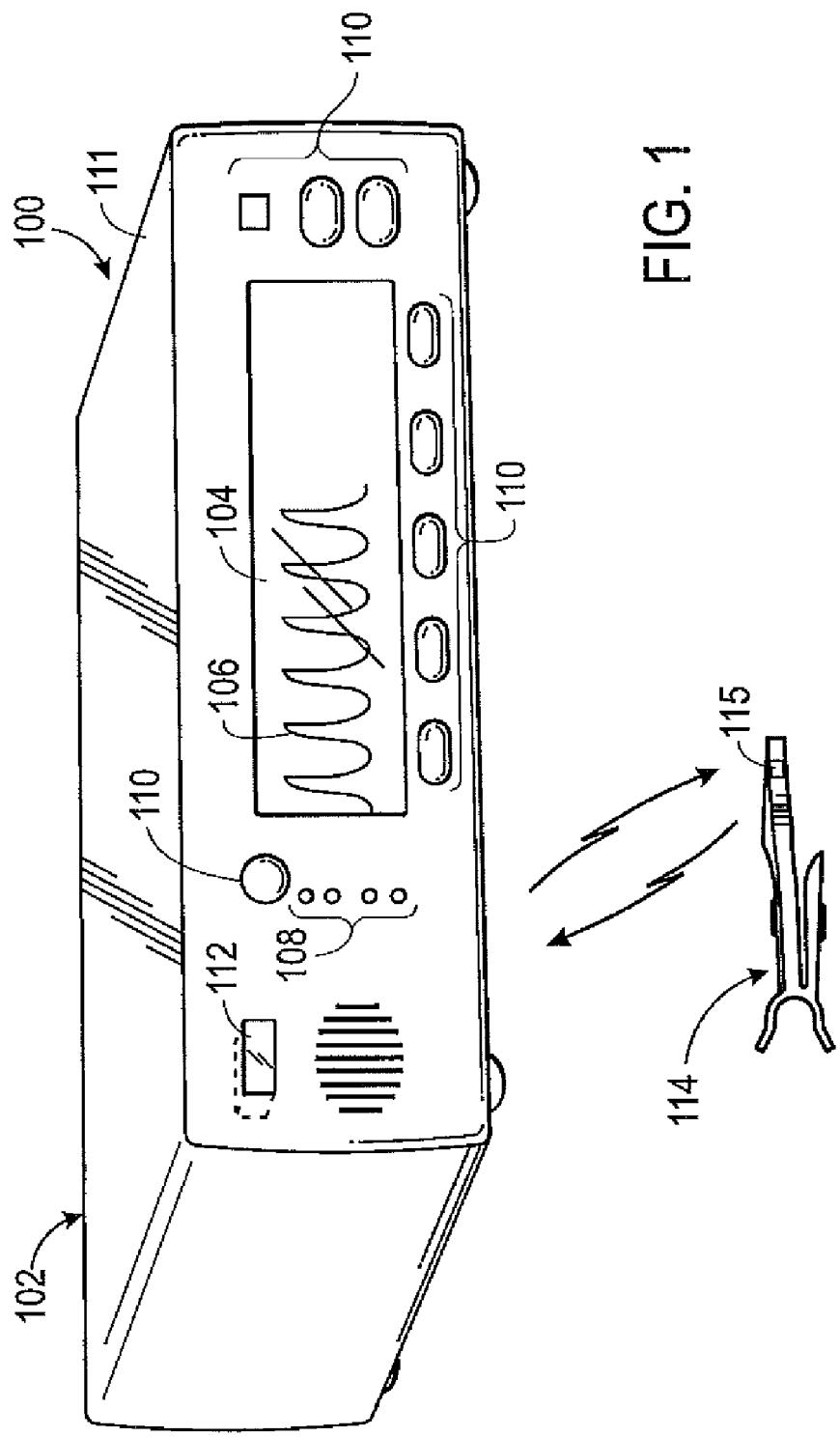
FIG. 1 illustrates a perspective view of a wireless power system including an electronic device, such as a pulse oximeter, in accordance with an embodiment.

Turning to FIG. 1, a perspective view of a medical device is illustrated in accordance with an embodiment. The medical device may be a pulse oximeter 100. The pulse oximeter 100 may include a monitor 102, such as those available from Nellcor Puritan Bennett LLC. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a transceiver 112. The transceiver 112 may allow for wireless operation signals to be transmitted to and received from an external sensor 114. In this manner, the monitor 102 and the sensor 114 may communicate wirelessly. The sensor 114 may be of a disposable or a non-disposable type. Furthermore, the sensor 114 may obtain readings from a patient that can be used by the monitor 102 to calculate certain physiological characteristics such as the blood-oxygen saturation of hemoglobin in arterial blood, the volume of individual blood pulsations supplying the tissue, and/or the rate of blood pulsations corresponding to each heartbeat of a patient. As will be discussed in greater detail below, the sensor 114 may include a charging device 115, respectively, for harnessing of energy for use by the sensor 114.

Figure 2:
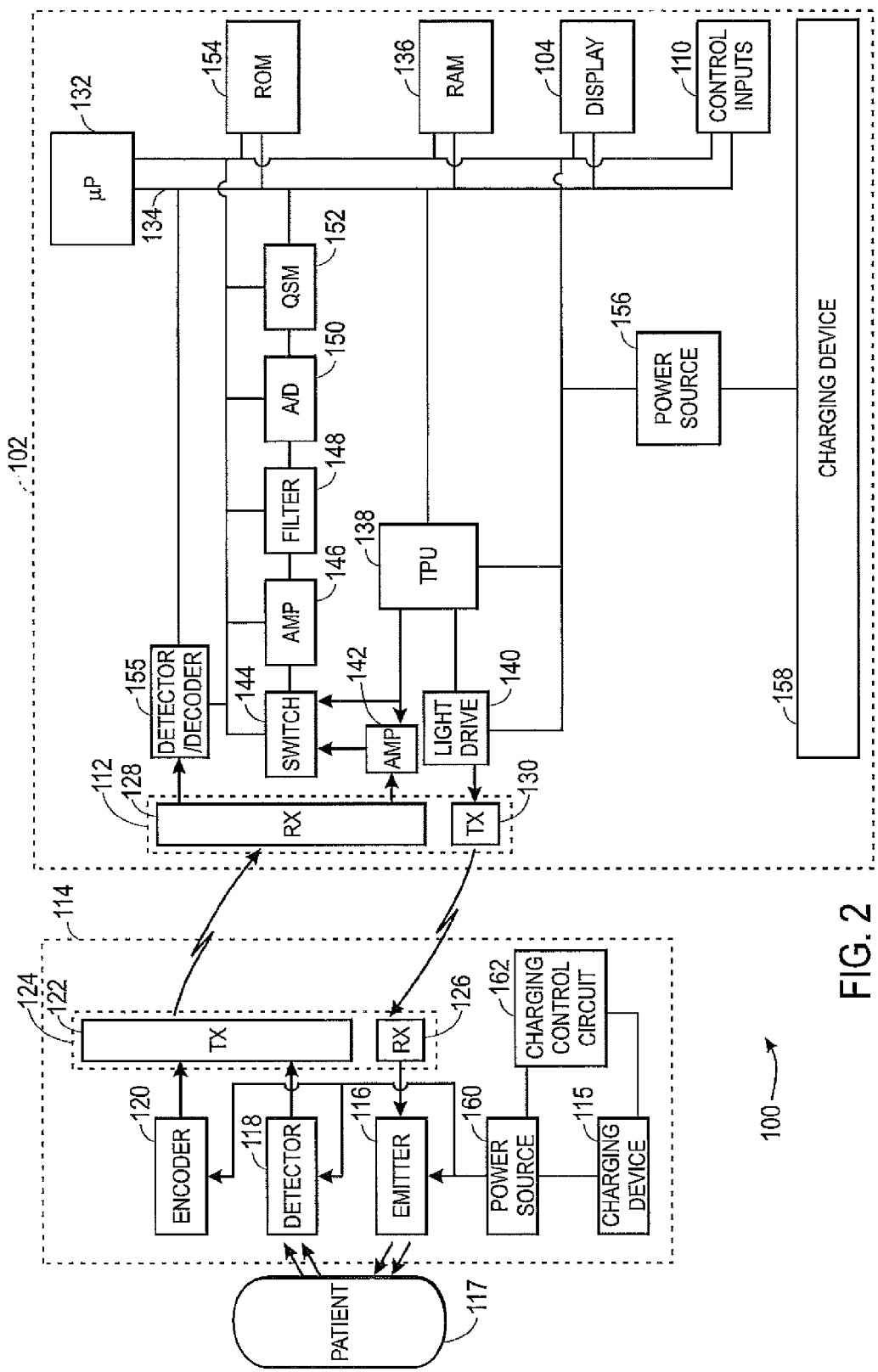
FIG. 2 illustrates a simplified block diagram of the pulse oximeter in FIG. 1, according to an embodiment.

Turning to FIG. 2, a simplified block diagram of the pulse oximeter 100 is illustrated in accordance with an embodiment. Specifically, certain components of the sensor 114 and the monitor 102 are illustrated in FIG. 2. As previously noted, the sensor 114 may include a charging device 115. The sensor 114 may also include an emitter 116, a detector 118, and an encoder 120. It should be noted that the emitter 116 may be capable of emitting at least two wavelengths of light, e.g., RED and infrared (IR) light, into the tissue of a patient 117 to calculate the patient's 117 physiological characteristics, where the RED wavelength may be between about 600 nanometers (nm) and about 700 nm, and the IR wavelength may be between about 800 nm and about 1000 nm. Alternative light sources may be used in other embodiments. For example, a single wide-spectrum light source may be used, and the detector 118 may be capable of detecting certain wavelengths of light. In another example, the detector 118 may detect a wide spectrum of wavelengths of light, and the monitor 102 may process only those wavelengths which are of interest for use in measuring, for example, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. Additionally, the encoder 120 may include information relating to the proper charging of the sensor 112. The encoder 120 may, for instance, be a memory on which one or more of the following information may be stored for communication to the monitor 102; the type of the sensor 114; the wavelengths of light emitted by the emitter 116; the proper calibration coefficients and/or algorithms to be used for calculating the patient's 117 physiological characteristics; and/or information regarding a charging device for the sensor 114. The sensor 114 may be any suitable physiological sensor, such as those available from Nellcor Puritan Bennett LLC.

Signals from the detector 118 and the encoder 120 if utilized) may be transmitted to the monitor 102 via a transmitter 122 that may be located in a transceiver 124. The transceiver 124 may also include a receiver 126 that may be used to receive signals form the monitor 102. As may be seen, the receiver 126 may transmit received signals to the emitter 116 for transmission to a patient 117. The transmitter 122 may receive signals from both the detector 118 and the encoder 120 for transmission to the monitor 102. As previously described, the signals used in conjunction with the emitter 116 and the detector 118 may be utilized for the monitoring of physiologic parameters of the patient 117 while the signals from the encoder may contain information about the sensor 114 to allow the monitor 102 to select appropriate algorithms and/or calibration coefficients for calculating the patient's 117 physiological characteristics.

As previously discussed, the monitor 102 may include a transceiver 112. The transceiver 112 may include a receiver 128 and a transmitter 130. The receiver 128 may receive transmitted signals from the transmitter 122 of the sensor 114 while the transmitter 130 of the monitor 102 may operate to transmit signals to the receiver 126 of the sensor 114. In this manner, the sensor 114 may wirelessly communicate with the monitor 102 (i.e., the sensor 114 may be a wireless sensor 114). The monitor 102 may further include one or more processors 132 coupled to an internal bus 134. Also connected to the bus may be a RAM memory 136 and the display 104. A time processing unit (TPU) 138 may provide timing control signals to light drive circuitry 140, which controls (e.g., via the transmitter 130), when the emitter 116 is activated, and if multiple light sources are used, the multiplexed timing for the different light sources. TPU 138 may also control the gating-in of signals from detector 118 through an amplifier 142 and a switching circuit 134. The amplifier 142 may amplify, for example, the signals from the detector 118 received at the receiver 128. The TPU 138 may control the gating-in of signals from detector 118 through an amplifier 142 to insure that the signals are sampled at the proper time, which may depend at least in part upon which of multiple light sources is activated, if multiple light sources are used. The received signal from the detector 118 may be passed through an (optional) amplifier 146, a low pass filter 148, and an analog-to-digital converter 150 for amplifying, filtering, and digitizing the electrical signals the from the sensor 114. The digital data may then be stored in a queued serial module (QSM) 152, for later downloading to RAM 136 as QSM 152 fills up. In an embodiment, there may be multiple parallel paths of separate amplifier, filter, and A/D converters for multiple light wavelengths or spectra received.

In an embodiment, based at least in part upon the received signals corresponding to the light received by detector 118, processor 122 may calculate the oxygen saturation using various algorithms. These algorithms may use coefficients, which may be empirically determined, and may correspond to the wavelengths of light used. The algorithms may be stored in a ROM 154 and accessed and operated according to processor 122 instructions. The monitor 102 may also include a detector/decoder 155 that may receive signals (via the receiver 128) from the encoder 120. The detector/decoder 155 may, for instance, decode the signals from the encoder 120 and may provide the decoded information to the processor 132. The decoded signals may provide information to the processor such as the type of the sensor 114 and the wavelengths of light emitted by the emitter 116 so that proper calibration coefficients and/or algorithms to be used for calculating the patient's 117 physiological characteristics may be selected and utilized by the processor 132.

The monitor 102 may also include a power source 156 that may be used to transmit power to the components located in the monitor 102. In one embodiment, the power source 156 may be one or more batteries, such as a rechargeable battery. The battery may be user-removable or may be secured within the housing of the monitor 102. Use of a battery may, for example, allow the oximeter 100 to be highly portable, thus allowing a user to carry and use the oximeter 100 in a variety of situations and locations. Additionally, the power source 156 may include AC power, such as provided by an electrical outlet, and the power source 156 may be connected to the AC power via a power adapter through a power cord (not shown). This power adapter may also be used to directly recharge one or more batteries of the power source 156 and/or to power the pulse oximeter 100. In this manner, the power adapter may operate as a charging device 158.

The sensor 114 may also include a charging control circuit 162, which may, for example, allow for the adaptive control of wireless energy harvested from the charging device 115 for use in the power source 160 of the sensor 114. In one embodiment, the power source 160 may be one or more batteries, such as a rechargeable battery that may be user-removable or may be secured within the housing of the sensor 114. Alternatively, the power source 160 may be one or more capacitors for storage of charge. The charging control circuit 162 may, for example, include a processing circuit that may determine the current level of charge remaining in the power source 160, as well as the current amount of power being harvested by the charging device. For example, the charging control circuit 162 may determine if the charging device 115 is generating too little power to charge the power source 160. In response to determining that the charging device 115 is generating too little power to charge the power source 160 and that the power source 160 is low on power, the charging control circuit 162 may generate an error signal that may be transmitted to the monitor 102 for generation of a corresponding error message for display on the display 104 of the monitor 102 by, for example, the processor 132. The error message may indicate to a user that the sensor 102 is low on power and may also direct the user to take action, such as changing the power source 160 (i.e., installing new batteries), charging the power source 160 (i.e. by plugging the sensor 102 into a charging unit or into an electrical outlet via a power adapter). Alternatively, the error message may indicate to a user that the recharging system of the sensor is potentially malfunctioning, and may direct the user, for example, to replace the sensor 114. In one embodiment, the error message may be generated when the charging control circuit 162 determines that the power source 160 has reached a certain charge level, for example 20% of the total charge remains in the power source 160. Additionally, as described below in greater detail, the charging control circuit 162 may also include conversion translation circuitry, such as a rectifier circuit, for conversion of alternating current generated via the charging device 115 into direct current. Thus, in one embodiment, the generated electricity may be passed through a rectifier circuit, which may be located in, for example, the charging control circuit 162, which may translate the alternating current the charging device into direct current. The rectifier circuit may, for example, be a full wave rectifier made up of, for example, diodes. The rectification of the electricity by the rectifier circuit may also include smoothing the output of the rectifier circuit. A filter, such as a reservoir capacitor, may be used to smooth the output of the rectifier circuit prior to its transmission to the power storage device 160.

The charging device 115 may be one of a multitude of energy harvesting components that utilize, for example, piezoelectric energy generation techniques. Through use of these techniques, power may be harvested, for example, through airflow (i.e. air movement) across the charging device 115, and utilized to directly recharge one or more batteries (or capacitors) of the power source 160 and/or to power the sensor 114. FIG. 3 illustrates a first embodiment of the charging device 115.

The charging device 115 may include a plurality of energy harvesters 164 extending radially 166 from a substrate 168. In one embodiment, the substrate 168 may be an insulative material, such as a ceramic, or a may be a semiconductor material, such as intrinsic silicon. The energy harvesters 164 may be grown onto the substrate 168 as cylindrical shaped wires. It should be noted that one or more energy harvesters 164 may be utilized in conjunction with one another and that the energy harvester 164 may be sized to be imbedded into the sensor 114 with the energy harvesters 164 extending outwards from the external surface of the sensor 114. Additionally or alternatively, the energy harvester 164 may be attached to the surface of the sensor 114. In one embodiment, the charging device 115, as well as the energy harvesters 164, may be, for example, microelectromechanical systems (MEMS) and/or nanoelectromechanical systems (NEMS) made up of components sized between approximately 100 nanometers and 100 micrometers. However, the energy harvester 164, as well as the components that make up the energy harvester 164, may also be larger than MEMS and NEMS described above.

Returning to the energy harvesters 164, as described above, the energy harvesters 164 may be cylindrical in shape. For example, the diameter 170 of the energy harvesters 164 may be between approximately 100 to 800 nanometers while the length 172 of the energy harvesters 164 may be between approximately 1 to 10 micrometers. Furthermore, the energy harvesters 164 may be arranged across the substrate 168 with approximately between 200 to 1000 nanometers between each energy harvester 164. Furthermore, the energy harvesters 164 may be made up of piezoelectric material. For example, materials utilized to create the energy harvesters 164 may include Zinc Oxide (ZnO), Arium titanate ($BaTiO_3$), Lead titanate ($PbTiO_3$), Lead zirconate titanate (commonly known as PZT), and/or potassium niobate ($KNbO_3$).

Accordingly, the energy harvesters 164 may operate as piezoelectric wires, with the ability to generate an electric potential in response to applied mechanical stress. Accordingly, the characteristics of the piezoelectric materials in the energy harvesters 164 may cause current to be generated from the energy harvester 164 as the energy harvester 164 is moved by forces such as airflow passing across the energy harvesters 164. This current may be captured as illustrated in FIGS. 4A and 4B.

FIGS. 4A and 4B illustrate a single (piezoelectric) energy harvester 164 of the charging device 115 in a first and a second position, respectively. As may be seen in FIG. 4A, the energy harvester 164 may be in a first straightened position. This position may represent a rest position of the energy harvester 164 when no forces, such as airflow, are sufficiently acting upon the energy harvester 164. Accordingly, in the rest position illustrated in FIG. 4A, no energy is being harvested for use by, for example, the power source 160. Also illustrated are a first contact 174 and a second contact 176, as well as leads 178 and 180. The contacts 174 and 176 may be utilized to harvest current generated by the potential difference created by when a force causes the energy harvester 164 to bend. This current may be transmitted across leads 178 and 180 along substrate 168 to power source 160 and/or charging control circuit 162 as harvested energy.

FIG. 4B illustrates the energy harvester 164 in a bent position under the influence of a force, such as airflow, as illustrated by directional arrow 182. The force along line 182 may cause the piezoelectric material in the energy harvester 164 to bend, thus generating a potential difference in the energy harvester 164. This may cause a current to be generated and passed through, for example, lead 178 and/or lead 180 along substrate 168 to power source 160 and/or charging control circuit 162 as harvested energy. Voltages harvested in this manner from each energy harvester 164 may range from approximately 1 millivolt to 25 millivolts while the current generated may be approximately 50 picoamps to 200 picoamps.

Furthermore, a characteristic of the piezoelectric material in the energy harvester 164 is that the greater the deformation of the piezoelectric material, the larger the potential difference generated in the energy harvester 164. Accordingly, by increasing the surface area of the energy harvesters 164 exposed to airflow, more force may be harvested from airflow causing the energy harvesters 164 to deform (i.e. bend) at a greater rate. In one embodiment, an uppermost portion 184 of the energy harvesters 164 may be modified to increase air resistance. This portion 184 of the energy harvesters 164 may be, for example, equivalent to approximately 5, 10, 20, 30, 40, 50, 60, 70, 80, 90, or 100% of the length 172 of the energy harvester 164. In another embodiment, the uppermost portion 184 of the energy harvesters 164 may be approximately 25% or 33% of the total length 172 of the energy harvesters 164, as measured from the top portion 185 of the energy harvester 164. Additionally, the uppermost portion 184 of the energy harvester 164 may have a diameter approximately equivalent to the diameter 170 of the energy harvester 164. Alternatively, the uppermost portion 184 of the energy harvester 164 may have a diameter greater or less than the diameter 170 of the energy harvester 164. Furthermore, the uppermost portion 184 of the energy harvester 164 may be cylindrical similar to the energy harvester 164. Alternatively, the uppermost portion 184 of the energy harvester 164 may have a different shape than the energy harvester 164. Embodiments of various shapes that may be utilized for the uppermost portion of the energy harvester 164 are illustrated in FIGS. 5A, 5B, and 5C.

Figure 5A:
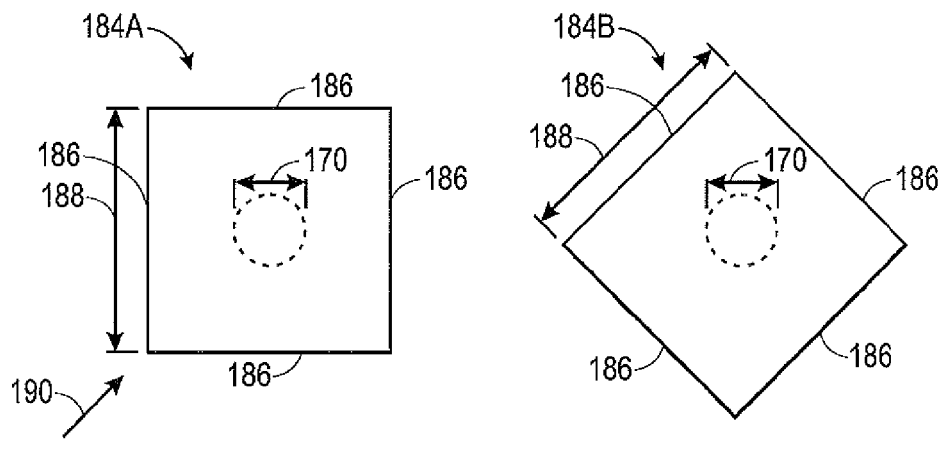
FIG. 5A illustrates an embodiment of the piezoelectric element of FIGS. 3A and 3B, in accordance with an embodiment.

FIG. 5A illustrates a top view of a first embodiment of shaped uppermost portions 184A and 184B of two energy harvesters 164. As illustrated, uppermost portions 184A and 184B with changed shapes that allow for an increase in the surface area of the energy harvesters 164 exposed to airflow. The energy harvesters 184A and 184B may each be made from piezoelectric material making up the energy harvesters 164; however, they may be sized and shaped differently than the cylindrical shape of the energy harvesters 164 described above. For example, uppermost portions 184A and 184B may be box-shaped with four sides 186. Each of the four sides 186 may be equivalent in length or one or more of the sides 186 may be a different length than the remaining sides 186. Furthermore, the length 188 of the sides 186 may be different than the diameter 170 of the energy harvester 164. In one embodiment, the length 188 of one or more of the sides 186 may be approximately 1.25, 1.5, 1.75, 2, 2.5, or greater times the diameter 170 of the energy harvester 164. In another embodiment, the sides 186 may have a length 188 approximately equal in length to the diameter 170 of the energy harvester 164.

Additionally, as illustrated in FIG. 5A, the uppermost portions 184A and 184B of two energy harvesters 164 may be offset with respect to one another. For example, the uppermost portion 184B may be aligned with approximately a 45 degree offset with respect to the alignment of upper portion 184A (i.e., rotated 45 degrees with respect to the position of upper portion 184A). In other embodiments, the uppermost portions 184B may be aligned with approximately a 10, 20, 30, 40, 50, 60, 70, or 80 degree offset with respect to the alignment of upper portion 184A. By altering the alignment of the upper portions 184A and 184B, airflow from a plurality of directions may be harvested more efficiently. For example, airflow along directional line 190 may encounter upper portion 184A at a corner between two sides 186, which may cause the air to tend to flow around upper portion 184A. However, when the same airflow along directional line 190 encounters upper portion 184B, it may do so flush with side 186, which may act as a larger air resistance surface than the corner previously discussed with respect to upper portion 184A. This larger air resistance surface may allow upper portion 184B to cause the energy harvester 164 associated with the upper portion 184B to bend at a greater rate than the energy harvester 164 associated with the upper portion 184A. Additionally, it should be noted that this pattern of offsetting upper portions 184A and 184B may be continued across a portion or the entirety of substrate 168 described above.

Figure 5B:
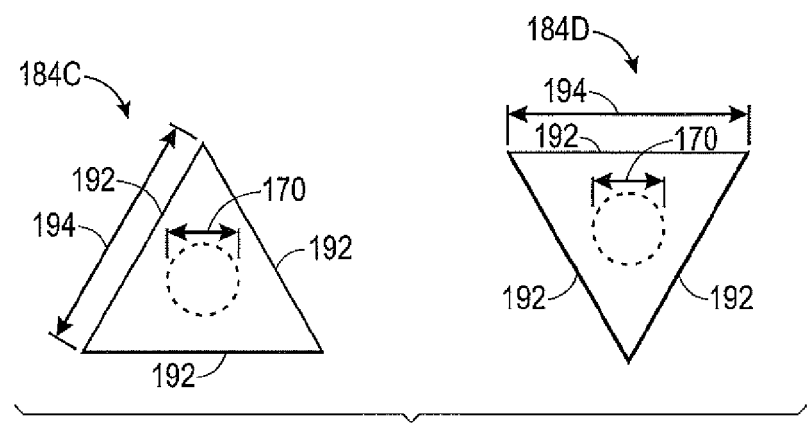
FIG. 5B illustrates a second embodiment of the piezoelectric element of FIGS. 3A and 3B, in accordance with an embodiment.
Figure 5C:
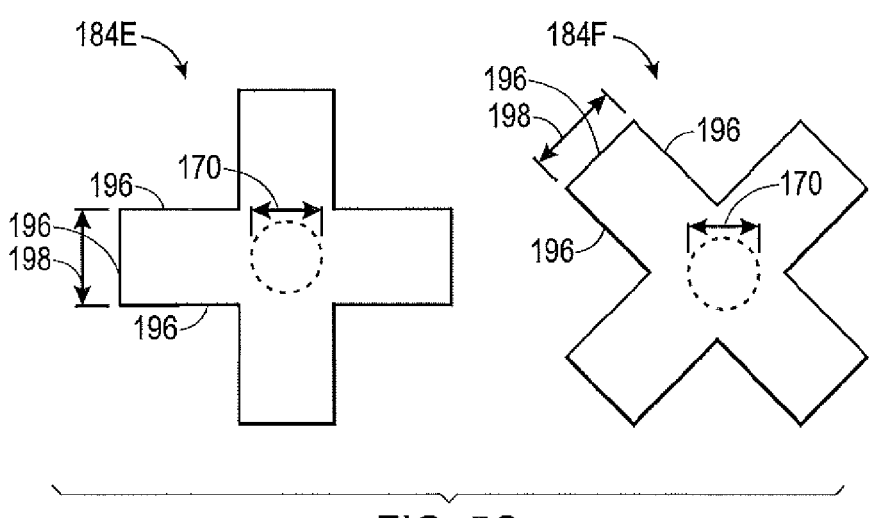
FIG. 5C illustrates a third embodiment of the piezoelectric element of FIGS. 3A and 3B, in accordance with an embodiment.

FIG. 5B illustrates a top view of another embodiment of shaped uppermost portions 184C and 184D of two energy harvesters 164. The energy harvesters 184C and 184D may each be made from piezoelectric material making up the energy harvesters 164; however, they may be sized and shaped differently than the cylindrical shape of the energy harvesters 164 described above. For example, uppermost portions 184A and 184B may be triangular-shaped with three sides 192. Each of the three sides 192 may be equivalent in length or one or more of the sides 192 may be a different length than one or more of the remaining sides 192. Furthermore, the length 194 of the sides 192 may be different than the diameter 170 of the energy harvester 164. In one embodiment, the length 194 of one or more of the sides 192 may be approximately 1.25, 1.5, 1.75, 2, 2.5, or greater times the diameter 170 of the energy harvester 164. In another embodiment, the sides 192 may have a length 194 approximately equal in length to the diameter 170 of the energy harvester 164.

Additionally, as illustrated in FIG. 5B, the uppermost portions 184C and 184D of two energy harvesters 164 may be offset with respect to one another. For example, the uppermost portion 184D may be aligned with approximately a 180 degree offset with respect to the alignment of upper portion 184C (i.e., rotated 180 degrees with respect to the position of upper portion 184C). In other embodiments, the uppermost portions 184D may be aligned with approximately a 30, 60, 90, 120, or 150 degree offset with respect to the alignment of upper portion 184C. As described above, by altering the alignment of the upper portions 184C and 184D, airflow from a plurality of directions may be harvested more efficiently. Accordingly, the pattern of offsetting upper portions 184C and 184D may be continued across a portion or the entirety of substrate 168 described above.

FIG. 5C illustrates a top view of an embodiment of shaped uppermost portions 184E and 184F of two energy harvesters 164. The energy harvesters 184E and 184F may each be made from piezoelectric material making up the energy harvesters 164; however, they may be sized and shaped differently than the cylindrical shape of the energy harvesters 164 described above. For example, uppermost portions 184E and 184F may be cross-shaped with twelve sides 196. Each of the sides 196 may be equivalent in length or one or more of the sides 196 may be a different length than one or more of the remaining sides 196. Furthermore, the length 198 of the sides 196 may be different than the diameter 170 of the energy harvester 164. In one embodiment, the length 194 of one or more of the sides 192 may be approximately 1.2, 1.4, 1.6, 1.8, 2, or greater times the diameter 170 of the energy harvester 164. In another embodiment, the sides 196 may have a length 198 approximately equal in length to the diameter 170 of the energy harvester 164.

Additionally, as illustrated in FIG. 5C, the uppermost portions 184E and 184F of two energy harvesters 164 may be offset with respect to one another. For example, the uppermost portion 184F may be aligned with approximately a 45 degree offset with respect to the alignment of upper portion 184E (i.e., rotated 45 degrees with respect to the position of upper portion 184E). In other embodiments, the uppermost portions 184F may be aligned with approximately a 10, 20, 30, 40, 50, 60, 70, or 80 degree offset with respect to the alignment of upper portion 184E. As described above, by altering the alignment of the upper portions 184E and 184F, airflow from a plurality of directions may be harvested more efficiently. Accordingly, the pattern of offsetting upper portions 184E and 184F may be continued across a portion or the entirety of substrate 168 described above.

Figure 6:
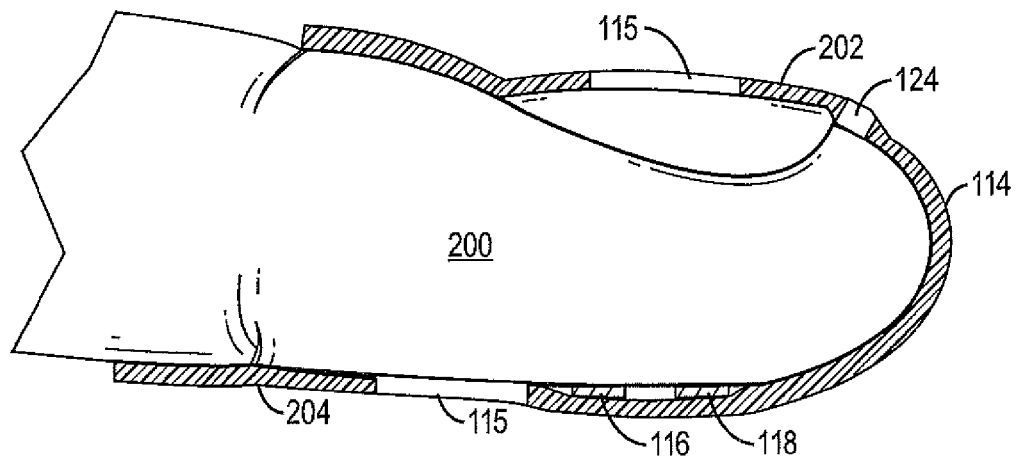
FIG. 6 illustrates a first placement of the charging device and sensor of FIG. 1, in accordance with an embodiment.

The location of the energy harvesters 164 of the charging device 115 may impact the amount of energy harvested by airflow. FIG. 6 illustrates various placement locations of one or more charging devices 115 in conjunction with a sensor 114. The sensor 114 may be utilized in conjunction with a finger 200 of a patient 117. As may be seen, the emitter 116 and the detector 118, as well as the transceiver 124 are illustrated as elements of the sensor 114. As depicted, the emitter 116 and detector 118 may be arranged in a reflectance-type configuration in which the emitter 116 and detector 118 are typically placed on the same side of the sensor site. Reflectance type sensors may operate by emitting light into the tissue (e.g., finger 200) and detecting the reflected light that is transmitted and scattered by the tissue. That is, reflectance type sensors detect light photons that are scattered back to the detector 118. The sensor 114 may alternatively be configured as a transmittance type sensor whereby the emitter 116 and detector 118 are typically placed on differing sides of the sensor site. In this manner, the detector 118 may detect light that has passed through one side of a tissue site to an opposite side of the tissue site.

As illustrated in both FIG. 6, the sensor 114 may also include one or more charging stations 115. The charging stations 115 may include piezoelectric energy harvesters 164, detailed above. In one embodiment, a charging station 115 may be located on a top side 202 of the sensor. Additionally and/or alternatively, a charging station 115 may be located on the bottom side 204 of the sensor 114. Each of these charging stations 115 may be integrated into the sensor 114, or affixed thereto. Furthermore, these charging stations 115 may operate independently, or may be electrically coupled to one another to increase the overall airflow that may be harvested for use by the sensor 114. Additionally, one or more charging stations 115 external to the sensor 114 may be utilized.

Figure 7:
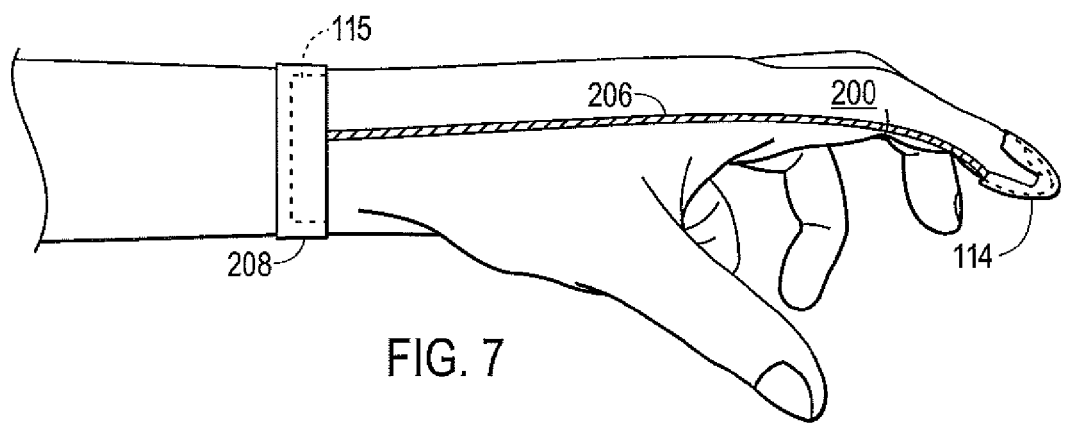
FIG. 7 illustrates a second placement of the charging device and sensor of FIG. 1, in accordance with an embodiment.

FIG. 7 illustrates an embodiment whereby the charging device 115 is located externally from the sensor 114. As illustrated, the charging device 115 may be attached to the sensor 114 via a lead 206. The lead 206 may be an electrical conductor, such as a power cable, that transmits harvested power to the sensor 114. The lead 206 may terminate with the charging device 115 which may be integrated into (or be attached to) a bracelet 208. The bracelet 208 may be, for example, a medical bracelet. Furthermore, the lead 206 may be connected to and separated from the charging device 115. That is, the lead 206 may be separable (i.e., releasable) from the charging device 115, the bracelet 208, and/or the sensor 114. Alternatively, the lead 206 may be permanently affixed to the charging device 115 and/or the bracelet 208. Regardless, by separating the charging device 115 from the sensor 114, more available area in the bracelet 208 may be available for harvesting of energy via patient 117 movement. That is, with greater area available for the charging device 115, a greater number of energy harvesters 164 may be utilized, thus increasing the overall amount of energy that may be harvested.

Figure 8:
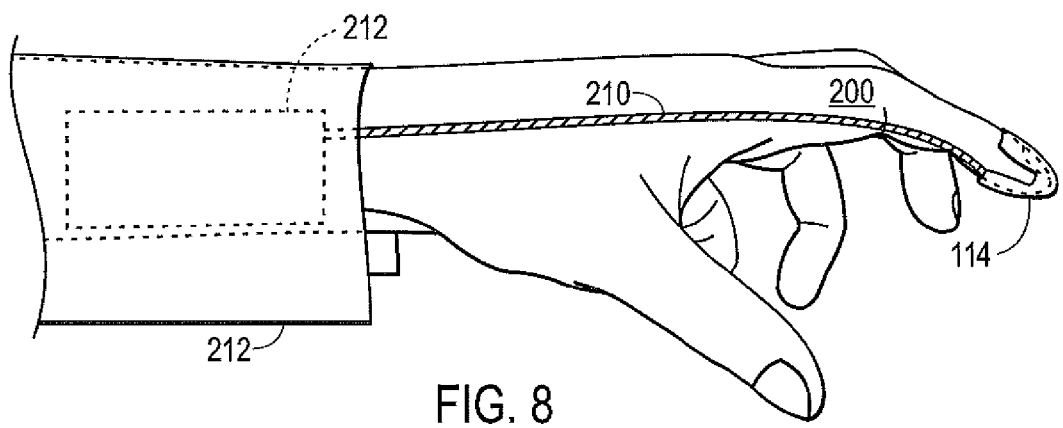
FIG. 8 illustrates a third placement of the charging device and sensor of FIG. 1, in accordance with an embodiment.

FIG. 8 illustrates a second embodiment whereby the charging device 115 may be located externally from the sensor 114. As illustrated, the charging device 115 may be attached to the sensor 114 via a lead 210. The lead 210 may be an electrical conductor, such as a power cable, that transmits power to the sensor 114 and may terminate with the charging device 115 which may be integrated into (or be attached to) a garment 212. Again, the lead 210 may be separable (i.e., releasable) from the charging device 115, the garment 212, and/or the sensor 114. The garment 212 may be, for example, a shirt or a sleeve of a shirt. The use of the a garment 212 to house the charging device 115 may allow for the charging device 115 to be expanded in size, or for more than one charging devices 115 to be utilized in conjunction, while still allowing for the garment 212 to be comfortably worn. Thus a greater number of energy harvesters 164 may be utilized, which may increase the overall amount of energy that may be harvested. Additionally, by utilizing a large area, such as the garment 212, movements of a patient 117 across a plurality of regions of the patient 117 may be utilized to harvest energy from. That is, movements in the chest, arms, etc. of the patient 117 may be translated into power for use by the sensor 114. In this manner, a greater number of movements of a patient 117 may be harvested into power for use with the sensor 114 relative to energy harvesters 164 located in the sensor 114.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A physiological medical sensor, comprising:
   one or more power generating piezoelectric structures disposed on an exterior portion of a medical sensor, wherein the one or more power generating piezoelectric structures generate power in response to air movement;
   one or more sensing components which, acting alone or in combination, are capable of generating data related to one or more physiological parameters; and
   wireless communication circuitry capable of wirelessly transmitting the data related to the one or more physiological parameters, wherein at least one of the one or more sensing components or the wireless communication circuitry are at least partially powered, directly or indirectly, by the one or more power generating piezoelectric structures.

2. The physiological sensor of claim 1, comprising an energy storing structure that is at least partially charged by the one or more power generating structures, wherein the one or more sensing components are at least partially powered by the energy storing structure.

3. The physiological sensor of claim 2 wherein the energy storing structure comprises a chargeable battery or a capacitor.

4. A power module for a physiological medical sensor, comprising:
   one or more power generating piezoelectric structures disposed on an exterior portion of a medical sensor, wherein the one or more power generating piezoelectric structures generate power in response to air movement; and
   a connector capable of releasably connecting to the physiological medical sensor, wherein the connector is capable of transmitting power generated by the one or more power generating piezoelectric structures to the physiological medical sensor when connected.

5. The power module of claim 4, comprising an energy storing structure that is at least partially charged by the one or more power generating structures.

6. The power module of claim 4, wherein the power module comprises a bracelet.

7. The power module of claim 6, wherein the one or more power generating structures are affixed to the bracelet.

8. The power module of claim 4, wherein the power module comprises a garment.

9. The power module of claim 8, wherein the one or more power generating structures are integrated into the garment.

10. The power module of claim 4, wherein the one or more power generating piezoelectric structures comprises a generally rectangular shaped member.

11. The power module of claim 4, wherein the one or more power generating piezoelectric structures comprises a generally triangular shaped member.

12. The power module of claim 4, wherein the one or more power generating piezoelectric structures comprises a generally cross shaped member.

13. A method for powering a wireless medical sensor, comprising the acts of:
   generating power via one or more power generating piezoelectric structures in response to air movement, wherein the one or more power generating piezoelectric structures is disposed on an exterior portion of a medical sensor; and
   providing the generated power from the one or more power generating piezoelectric structures to the medical sensor.

14. The method of claim 13, wherein the power is stored in a battery or capacitor prior to being provided to the sensor.

15. The method of claim 13, wherein the power is generated at a location separate from the sensor.

16. The method of claim 15, wherein the location separate from the sensor is at a bracelet or a garment worn by a patient.

17. The method of claim 13, comprising utilizing the power by the sensor to generate data related to one or more physiological parameters of a patient.

18. The method of claim 13, wherein the medical sensor is configured to be placed on a finger of a patient.

19. A monitoring system, comprising:
   a wireless medical sensor, comprising:
      a light generating component;
      a light detecting component capable of detecting light generated by the light generating component;
      a wireless transmitter capable of wirelessly transmitting a signal based on the light detected by the light detecting component;
      one or more power generating piezoelectric structures that generate power in response to air movement, wherein the one or more power generating piezoelectric structures is disposed on an exterior portion of the medical sensor, and wherein the generated power is provided to one or more of the light generating component, the light detecting component, or the wireless transmitter; and
   a monitor capable of receiving the signal.

20. The monitoring system of claim 19, wherein the power generating component is incorporated into the wireless sensor.

21. The monitoring system of claim 19, wherein the power generating component is separate from, but in communication with, the wireless sensor.

22. The monitoring system of claim 19, comprising an energy storage component capable of storing the generated power prior to the power being provided to one or more of the light generating component, the light detecting component, or the wireless transmitter.

* * * * *